US00PP09537P

United States Patent [19]

Meilland

[11] Patent Number: Plant 9,537

[45] Date of Patent: May 7, 1996

[54] SHRUB ROSE PLANT NAMED 'MEIRIENTAL'

[75] Inventor: Alain A. Meilland, Antibes, France

[73] Assignee: The Conard-Pyle Company, West Grove, Pa.

[21] Appl. No.: 495,314

[22] Filed: Jun. 27, 1995

[51] Int. Cl.[6] ..... A01H 5/00

[52] U.S. Cl. ..... Plt./1

[58] Field of Search ..... Plt./1, 6

[56] References Cited

U.S. PATENT DOCUMENTS

P.P. 8,199 4/1993 Moore ..... Plt./1

P.P. 8,235 5/1993 Warriner ..... Plt./1

*Primary Examiner*—Howard J. Locker

*Attorney, Agent, or Firm*—Burns, Doane, Swecker & Mathis

[57] ABSTRACT

A new and distinct variety of shrub rose plant is provided which forms attractive bright red blossoms. The blossoming is abundant and the plant reflowers well. The vegetation is vigorous and the plant possesses a climbing growth habit. The plant exhibits good disease resistance particularly with respect to Marssonina disease.

1 Drawing Sheet

SUMMARY OF THE INVENTION

The new variety of Shrub rose plant of the present invention was created by artificial pollination wherein two parents were crossed which previously has been studied in the hope that they would contribute the desired characteristics. The female parent (i.e., the seed parent) was the product of the pollination of the 'Centenaire de Lourdes' variety (non-patented in the United States) and the 'Picasso' variety (U.S. Plant Pat. No. 3,351). The male parent (i.e., the pollen parent) of the new variety was the 'Meihaiti' variety (non-patented in the United States). The parentage of the new variety can be summarized as follows:

('Centenaire de Lourdes'×'Picasso')×'Meihaiti'.

The seeds resulting from the above pollination were sown and small plants were obtained which were physically and biologically different from each other. Selective study resulted in the identification of a single plant of the new variety.

It is found that the new variety of shrub rose plant possesses the following combination of characteristics:

(a) forms attractive bright red blossoms,
(b) exhibits a propensity for climbing,
(c) exhibits a good ability to reflower,
(d) exhibits a good resistance to Marssonina disease, and
(e) is particularly suited for growing as ornamentation in the landscape.

The new variety meets the needs of the horticultural industry. It can be grown to particular advantage as attractive ornamentation in parks, gardens, public areas, and residential landscapes.

The characteristics of the new variety have been found to be homogeneous and stable and are strictly transmissible by asexual propagation carried out in France (e.g., by budding, grafting, and cuttage) from one generation to another.

The newe variety has been named the 'Meiriental' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were three years of age and were observed during June while budded on *Rosa froebelii* understock and growing outdoors at Le Cannet des Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of blooming;

FIG. 6 — illustrates a specimen of a open flower — plan view — obverse;

FIG. 7 — illustrates a specimen of a open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — upper surface;

FIG. 15 — illustrates a specimen of a leaf with five leaflets — under surface; and FIG. 16 — illustrates a specimen of a leaf with seven leaflets — upper surface.

DETAILED DESCRIPTION

Figures 1, 2, 3, 4, 5, 6, 7, 8, 9, 10, 11, 12, 13, 14, 15, 16:
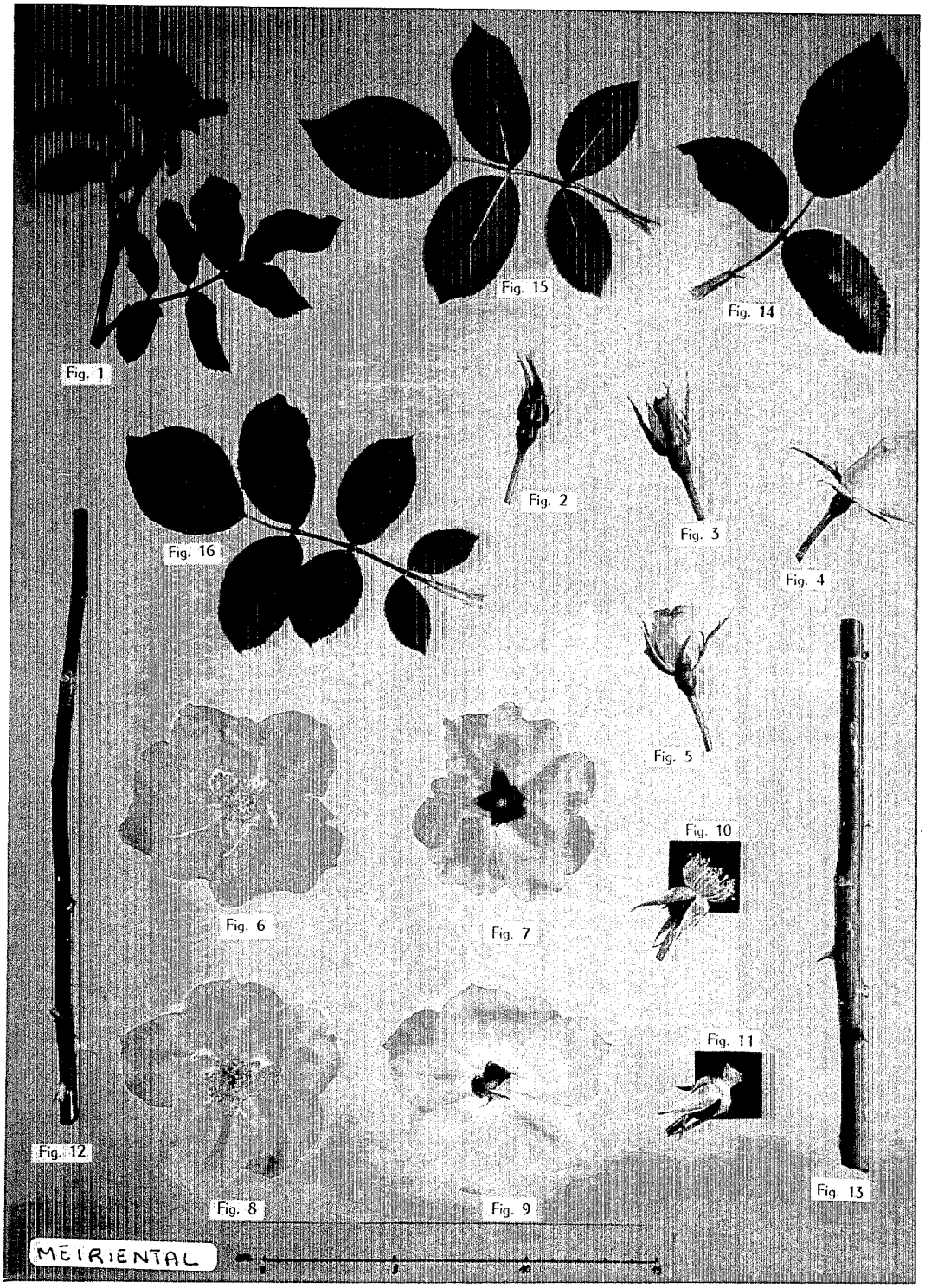

The chart used in the identification of the colors is that of the Royal Horticultural Society (R.H.S. Colour Chart). The terminology preceding the numbered reference to the chart has been added to indicate the corresponding color in more common terms. The description is based on the observation of three year-old specimens of the new variety during June while growing outdoors when budded on *Rosa froebelii* understock at Le Cannet des Maures, Var, France.

Class: Shurb.

Plant

*Height.*—Approximately 150 cm. on average at the end of the growing season.

*Habit.*—Climbing.

Branches:

*Color.*—Young stems: lettuce green, Yellow-Green Group 144A. Adult wood: medium green. Yellow-Green Group 148B.

*Thorms.*—Size: medium to large. Quantity: moderately numerous. Color: reddish on young stems and pinkish/greenish on adult wood as illustrated.

Leaves:

*Stipules.*—Adnate, pectinate, wide and linear.

*Petioles.*—Upper Surface: striped reddish on young foliage and medium green on adult foliage with more or less glandular edges. Under surface: light green and bear a few small thorns.

*Leaflets.*—Number: 3, 5 (most often), and 7. Shape: elliptic. Serration: simple and regular. Texture: leathery. General appearance: dense and semi-dull foliage. Color (young foliage): Upper surface: lettuce green, Yellow-Green Group 144A. Uder surface: lettuce green, Yellow-Green Group 144A. Color (adult foliage): Upper surface: dark green, Yellow-Green Group 146A. Under surface: light green, Yellow-Green Group 146C.

Inflorescence:

*Number of flowers.*—Usually one to five flowers per stem.

*Peduncle.*—Medium green, more or less maculated with reddish brown, and approximately 3 to 4 cm. in length on average.

*Sepals.*—Upper surface: tomentose, and greenish and more or less tinted with reddish coloration. Under surface: medium green and more or less tinted with reddish coloration, and the outer sepals commonly exhibit appendiculated edges.

*Buds.*—Shape: oblong. Length: approximately 2 to 3 cm. on average. Size: medium. Color when opening: Upper surface: Guardsman Red, Red Group 45B. Under surface: Turkey Red, Red Group 46C, suffused with Cardinal Red, Red Group 53C.

*Flower.*—Form: flat-cupped. Diameter: approximately 7 to 8 cm. on average. Color (when opening begins): Upper surface: Guardsman Red, Red Group 45B, suffused with Vermillion Red, Red Group 44A. Under surface: Turkey Red, Red Group 46C. Color (when blooming): Upper surface: Guardsman Red, Red Group 45B, suffused with Vermillion Red, Red Group 44A. Some petals may occasionally include streaks of lighter coloration (as illustrated). Under surface: Turkey Red, Red Group 46C, and with some lighter coloration at base (as illustrated). Color (at end of opening): Upper surface: Guardsman Red, Red Group 45B, suffused with Vermillion Red, Red Group 44A, and with lighter coloration at base (as illustrated). Under surface: Turkey Red, Red Group 46C. Fragrance: none. Lasting quality: long. Petal form: flattened and more or less indented on the top edge. Petal number: approximately 10 to 12 plus 2 or 3 incomplete petals on average. Petal drop: good. Stamen number: approximately 112 on average. Anthers: normal golden yellow in coloration. Filaments: dark fuchsine in coloration. Pistils: approximately 56 on average. Stigmas: normal and strawlike. Styles: dark fuchsine in coloration. Receptacle: medium green, more or less tinted with reddish coloration, smooth, and in longitudinal section in the shape of a pear.

Development:

*Vegetation.*—Vigorous.

*Blooming.*—Abundant and substantially continuous.

*Aptitude to bear fruits.*—Good.

*Resistance to diseases.*—Very good particularly with respect to Marssonina disease.

I claim:

1. A new and distinct variety of shrub rose plant characterized by the following combination of characteristics:

(a) forms attractive bright red blossoms, (b) exhibits a propensity for climbing, (c) exhibits a good ability to reflower, (d) exhibits a good resistance to Marssonina disease, and (e) is particularly suited for growing as ornamentation in the landscape;

substantially as herein shown and described.

* * * * *

MEIRIENTAL